United States Patent
Gubernick

[11] Patent Number: 5,871,527
[45] Date of Patent: Feb. 16, 1999

[54] MICROWAVEABLE MIXTURE AND HEATING PAD

[76] Inventor: Franklin L. Gubernick, 2540 N. Rising Star Tr., Tucson, Ariz. 85745

[21] Appl. No.: 787,938

[22] Filed: Jan. 23, 1997

[51] Int. Cl.⁶ .................................................. A61F 7/00
[52] U.S. Cl. ............................... 607/114; 62/4; 607/108; 126/204
[58] Field of Search ............................ 607/104, 108–112, 607/114; 126/204; 165/46; 62/4; 383/901

[56] References Cited

U.S. PATENT DOCUMENTS

| | | | |
|---|---|---|---|
| 4,756,299 | 7/1988 | Podella | 607/114 X |
| 5,190,504 | 3/1993 | Scatterday. | |
| 5,211,949 | 5/1993 | Salyer | 607/108 X |
| 5,534,020 | 7/1996 | Cheney, III et al. | 607/108 |
| 5,630,961 | 5/1997 | Salee | 607/108 X |
| 5,753,287 | 5/1998 | Chedid et al. | 426/93 X |

*Primary Examiner*—Jeffrey R. Jastrzab
*Assistant Examiner*—Ryan Carter
*Attorney, Agent, or Firm*—Franklin L. Gubernick

[57] ABSTRACT

A mixture designed to be heated by microwave energy and a container that can inwardly contain the mixture. The mixture is in a dry form and includes a quantity of salt that functions as a heat storage medium. The mixture further includes a quantity of starch material that functions to rapidly absorb microwave energy when it is subjected to microwaves in a conventional microwave oven. The starch material is in powder form and preferably coats the salt to thereby maximize the speed and efficiency of heat transfer between the two materials. The mixture may also include a powder lubricant that functions to improve the mixture's flowability. The container used to receive the microwaveable mixture is preferably flexible and may be manufactured from a fabric, plastic or rubber material. The container may be in the form of a pad or ball and includes a least one inner cavity that contains a quantity of the microwaveable mixture. When a ball-shaped container is employed, the container is preferably sized to enable it to be handheld and squeezed.

18 Claims, 1 Drawing Sheet

MICROWAVEABLE MIXTURE AND HEATING PAD

This application claims the benefit of U.S. Provisional Application Ser. No. 60/010,685 filed Jan. 26, 1996.

FIELD OF THE INVENTION

The invention is in the field of heatable mixtures and apparatus. More particularly, the invention is a dry, granular mixture that is designed to be contained within a flexible enclosure and heated in a conventional microwave oven. Once heated, the mixture retains the added heat for an extended period of time. In the preferred embodiment, the invention is employed for therapeutic use whereby the mixture is placed within a flexible enclosure to form a heating device. Also in the preferred embodiment, the mixture is fluent within the enclosure.

BACKGROUND OF THE INVENTION

Heating pads are commonly used by people to alleviate back pain and other similar pains that may result from pulled muscles and/or arthritis. There are a number of different forms of heating pads that are readily available, including electric heating pads and hot water bottles.

In recent years, microwaveable heating pads containing a sealed quantity of gel-type material or specially-designed beads have become available. When compared to an electric heating pad, these pads do not require the user to stay near an electrical outlet. The non-electrical pads also avoid the necessity of continually subjecting a user to low-level EMF exposure from the internal wiring used in an electric heating pad. When compared to a hot water bottle, the microwaveable pads are more convenient since they do not require the user to frequently fill, drain and then refill the bag with water.

While the gel-filled and bead-filled microwaveable pads provide the above-noted advantages over the prior art, each of these types of heating pads suffer certain disadvantages. A gel-filled heating pad is subject to leakage and can be overheated with detrimental results. In addition, if leakage should occur, the gel material may stain adjacent upholstery or clothing. In a bead-filled heating pad, the beads are relatively expensive and must occupy a significant volume to be effective. As a result of the latter condition, even when the beads are tightly packed, they still cause the heating pad to be quite thick. As a result, the pad may cause discomfort to the user.

SUMMARY OF THE INVENTION

The invention is a mixture that may be rapidly heated using a conventional microwave oven. In addition, the invention is a heating pad or device in which said mixture is placed with a container.

Once the mixture has been heated in a microwave oven, the mixture will retain the added heat for an extended period of time. In the preferred embodiment, the materials that make up the mixture are inexpensive and non-toxic.

A number of different powder/particulate materials are combined to form the microwaveable mixture. Firstly, there is a heat-retaining material that functions to retain added heat for an extended period of time. Secondly, there is a material that functions to rapidly absorb microwave energy and transform said energy into heat. In the preferred embodiment, the mixture also contains a dry lubricant powder that functions to increase the fluidity of the mixture and thereby allow the mixture to flow in a manner somewhat similar to a thick liquid.

For the heat-retaining material, a particulate salt material, such as salt crystals, is employed. This type of material has a low heat transfer rate and thereby will retain heat for an extended period of time. In the preferred embodiment, the salt crystals are very small and have a diameter of approximately 0.1 to 0.01 inches. While salt is capable of retaining heat for an extended period of time, salt is not readily heatable in a microwave oven.

To increase the heat absorbing capacity of the mixture, a material that is capable of being rapidly heated in a conventional microwave oven is mixed with and substantially coats the particulate salt. In the preferred embodiment, the heat absorbing material is a starch in powder form. Either a pure starch or a powder in which starch is a major component, such as conventional baking powder, may be employed. When the microwaveable mixture is subjected to high levels of microwave energy, the starch (or starch containing material) will readily absorb the microwave energy and transform said energy into heat. The heat-absorbing material preferably also has a high heat transfer rate. The close contact between the starch (or starch containing material) and the salt material enables the heat to be rapidly transferred from the starch material to the salt material.

While not absolutely necessary to the function of the mixture, a dry lubricant such as powdered talc may be combined with the other materials of the mixture. The talc functions to make the microwaveable mixture more fluent. As a result, a heating pad containing the mixture will be quite flexible and will easily conform to the contours of a user's body. In addition, the increased fluidity of the mixture will make the pad feel relatively soft.

In one embodiment of a heating pad in accordance with the invention, the pad consists of a container filled with the microwaveable mixture. The container is made of a flexible, non-porous material and has a shape substantially identical to that of a conventional hot water bottle. In the preferred embodiment of the invention, the container is made of a material that is not readily heated by microwave energy.

In a second embodiment of a heating pad in accordance with the invention, the pad consists of a container fashioned from a cloth or other flexible fabric material. The container has one or more interior cavities filled with the previously described microwaveable mixture.

In a third embodiment of the invention, a heatable device is formed in which the microwaveable mixture is contained within a multi-layered resilient housing. The device preferably has a shape similar to that of a ball and is sized to enable it to be comfortably grasped by a user's hand. In this manner, a user who has arthritis can hold the device in one hand after the device has been heated in a conventional microwave oven. Heat from the mixture will then penetrate the housing and enter the user's hand. The heated device can also be squeezed like an exercise grip to exercise the user's fingers while applying heat to said fingers.

DETAILED DESCRIPTION OF THE DRAWINGS

Figure 1:
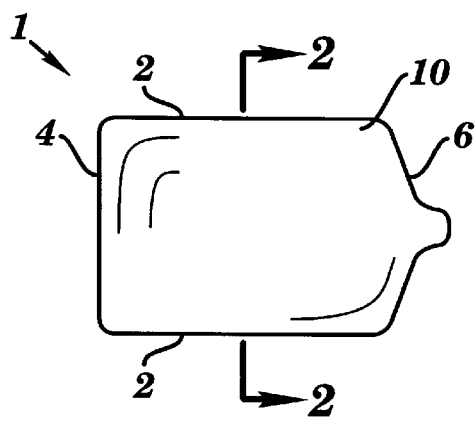
FIG. 1 provides a top view of a first embodiment of a heating pad in accordance with the invention.
Figure 2:
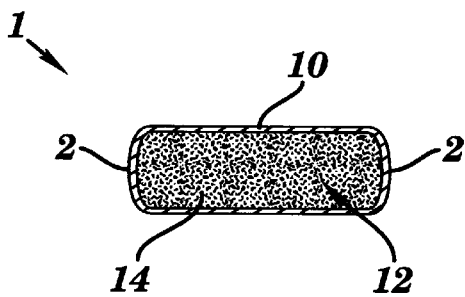
FIG. 2 shows a cross-sectional view of the embodiment shown in FIG. 1 taken at the plane labeled 2—2.

Referring now to the drawings in greater detail, wherein like reference characters refer to like parts throughout the several figures, there is shown by the numeral 1 a first embodiment of a heating pad in accordance with the invention.

The heating pad 1 is in the form of a relatively flat body that has sides 2 and closed first and second ends, 4 and 6 respectively. The pad includes a flexible outer housing 10 that is preferably made from a plastic or rubber material. In the preferred embodiment, pad 1 is similar in size and shape to a conventional hot water bottle (approximately 10 inches long by 7 inches wide by 0.5 inches thick) with the exception that the pad does not have a stopper structure to allow the entry or exit of water.

The outer housing 10 surrounds an interior area 12 that contains a microwaveable mixture 14 made up of a combination of dry particles and powder. During the manufacturing process, the mixture 14 is placed within the body through an end-located hole (not shown). The hole is closed by heat-sealing or other conventional closure methods immediately after the mixture has been placed within the body. Any excess air located within area 12 is purged prior to the final sealing of the housing.

The mixture 14 is preferably a combination of materials that have separate, distinct functions. The materials are preferably inexpensive and non-toxic.

The first ingredient of the mixture 14 is a material that does not readily absorb microwave energy but has a high capacity for retaining heat once it has been heated. In the preferred embodiment, this heat retaining material is a salt in particulate form such as common table salt.

The second ingredient of the mixture 14 is a material that readily absorbs microwave energy and transforms said energy into heat. Once mixed with the heat-retaining material, the energy-absorbing material will become in close contact with the previously described heat-retaining material so that it can transfer its heat quickly and efficiently to the heat-retaining material. Starch in powder form or a material having starch as a major component is preferably employed as the energy-absorbing material. This material is not only capable of being rapidly heated in a microwave oven, but will tend to coat the heat-retaining material to thereby enable the desired rapid transfer of heat to said material. In the preferred embodiment, baking powder having starch as a major ingredient is employed as the energy-absorbing material. An advantage to using baking powder in lieu of a pure starch, such as corn starch, is that baking powder also includes non-caking agents that increase the ability of the energy-absorbing material to mix with and coat the heat retaining material (salt particles).

An optional third ingredient of the mixture 14 is a dry lubricant in powder form. The lubricant functions to increase the fluidity of the mixture so that the mixture can be manually distributed within the pad in much the same manner as water may be re-distributed within a hot water bottle. This enables the heating pad to rapidly and easily conform to the contours of the user's body when it is pressed into contact with said body. The increased fluidity of the mixture also provides the pad with a soft feel. In the preferred embodiment, talc or talcum powder is employed as the lubricating material. It should be noted that if mixture 14 is made without an added dry lubricant, the mixture will still be fully functional but may compact and be more difficult to distribute within the housing.

Through testing, it was observed that the best compromise between heat-up time (the amount of time required to heat the mixture in a microwave oven) and heat retention time (the amount of time the material would stay hot, once heated) was achieved in a mixture having 16 units of heat-retaining material mixed with approximately 1–3 units of energy-absorbing material. In this idealized mixture, one can add approximately 1–3 units of dry lubricant to provide the best fluidity without causing significant adverse effects on the mixture's performance. One can depart from the above-noted ratios if one desires to affect the performance of the mixture. For example, by increasing the proportion of energy-absorbing material, one will decrease the mixture's required heat-up time. However, this will cause the mixture's heat-retention time to decrease.

One example of a tested mixture 14 made in accordance with the invention and providing excellent results had the following volumetric proportions of ingredients:

approximately one cup of non-iodized table salt;

approximately 1/8 cup of baking powder; and approximately 1/8 cup of talcum powder.

The above ingredients were thoroughly mixed together and the following test was made. The mixture, at an initial temperature of approximately 75 degrees Fahrenheit, was placed in a 750 watt conventional microwave oven. The oven was then started at its high setting and the material was subjected to microwave energy for two minutes. At the end of this time period, the temperature of the material was measured and had increased to 134 degrees Fahrenheit. The material was then allowed to cool in a room having an ambient temperature of approximately 74 degrees Fahrenheit. After 30 minutes, the mixture's temperature was measured and had decreased to approximately 92 degrees Fahrenheit.

Figure 3:
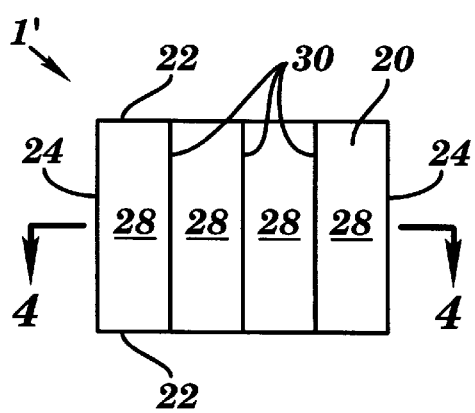
FIG. 3 provides a top view of a second embodiment of the invention.
Figure 4:
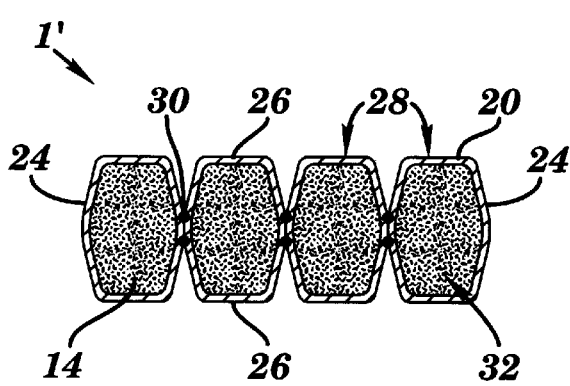
FIG. 4 shows a cross-sectional view of the embodiment shown in FIG. 3 taken at the plane labeled 4—4.

FIGS. 3 and 4 show a second embodiment of a heating pad 1' in accordance with the invention. In this embodiment, the pad includes a fabric outer housing 20 that is preferably made of either a cotton or ripstop nylon material. The housing has sides 22, ends 24 and top and bottom faces 26. The perimeter of the pad is sealed using sewn stitches. The pad itself is divided into a number of separate compartments 28 through the use of lines 30 of sewn stitches. The stitches pull together portions of the pad's top and bottom faces to thereby separate one compartment from another. Each of the formed compartments has its own interior area 32 that is filled with the microwaveable mixture 14. The lines 30 of stitches act like hinges to allow the separate compartments 28 of the pad to be movable relative to one another. This enhances the ability of the pad to bend and thereby conform to a user's body.

Figure 5:
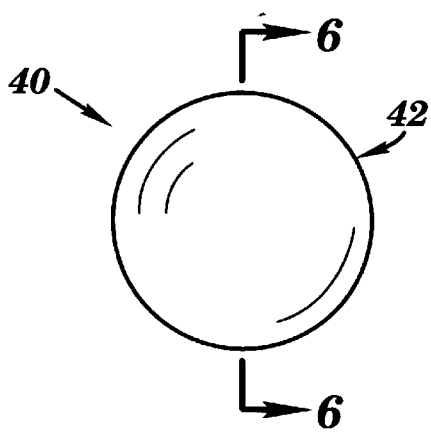
FIG. 5 provides a top view of a third embodiment of the invention.
Figure 6:
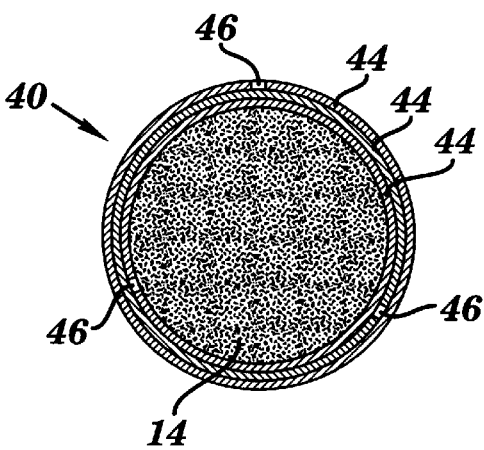
FIG. 6 shows a cross-sectional view of the embodiment shown in FIG. 5 taken at the plane labeled 6—6.

FIGS. 5 and 6 show a third embodiment of a heating device 40 in accordance with the invention. In this embodiment, the device has a substantially round shape and measures approximately two and one-half inches in diameter. The device includes a flexible outer housing 42 that is formed from a plurality of individual flexible sacks 44. Each sack is made of a resilient rubber material such as latex rubber and has a single opening 46. The sacks are nested together with their respective openings 46 offset from each other. Located within the housing is a compact mass of the microwaveable mixture 14. The use of a resilient material for the sacks 44 enables the device to be readily deformable and to function in the same manner as a conventional deformable handheld exercise device. However, unlike prior art hand exercise devices, the device 40 can be heated in a microwave oven to thereby enable the device to heat a user's hand as the user deforms the device.

It should be noted that while certain types of containers have been shown and described, other types of containers may be employed to inwardly contain the mixture 14. For example, non-flexible containers may be used if bending of the container will not be required.

The embodiments disclosed herein have been discussed for the purpose of familiarizing the reader with the novel aspects of the invention. Although preferred embodiments of the invention have been shown and described, many changes, modifications and substitutions may be made by one having ordinary skill in the art without necessarily departing from the spirit and scope of the invention as described in the following claims.

I claim:

1. A mixture of dry materials designed and adapted for use in a heating pad, wherein said dry mixture may be controllably heated through the application of microwave energy to said dry mixture, said mixture comprising:

a first dry material composed of salt crystals, wherein said material functions to retain heat, wherein when said material is subjected to a predetermined amount of microwave energy, said material will exhibit a first microwave energy absorption rate and then exhibit a first heat transfer rate; and a second dry material located in close contact with and at least partially coating the first dry material, wherein said second dry material is capable of absorbing microwave energy at a faster rate than the first dry material, wherein when said second dry material is subjected to said predetermined amount of microwave energy, said second dry material will exhibit at microwave energy absorption rate that is greater than that of the first dry material and thereby functions to heat said first dry material.

2. The mixture of claim 1 wherein the second dry material is primarily composed of a starch in powder form.

3. The mixture of claim 1 wherein the second dry material is baking powder.

4. The mixture of claim 1 further comprising a third dry material, wherein said third dry material is a lubricant in powder form and functions to increase the flowability of the mixture.

5. The mixture of claim 6 wherein the third dry material at least partially includes talc.

6. A microwaveable heating device designed and adapted for use as a heating pad, said device comprising:

a dry fill material designed and adapted to be heated through the application of microwave energy to said dry mixture, wherein said mixture includes a first dry material composed of salt crystals, wherein said first dry material functions to retain heat, wherein when said first dry material is subjected to a predetermined amount of microwave energy, said first dry material will exhibit a first microwave energy absorption rate and then exhibit a first heat transfer rate, and wherein said fill material also includes a second dry material that physically contacts the first dry material, wherein said second dry material is capable of absorbing microwave energy at a faster rate than the first dry material, wherein when said second dry material is subjected to said predetermined amount of microwave energy, said second dry material will exhibit a microwave energy absorption rate that is greater than that of the first dry material and thereby functions to heat said first dry material; and a housing having an inner cavity that is substantially filled with said fill material.

7. The device of claim 6 wherein the second dry material of the fill material is in the form of a starch in powder form.

8. The device of claim 6 wherein the housing is made from a plastic material.

9. The device of claim 6 wherein the housing is made from a fabric material.

10. The device of claim 6 wherein the housing includes a plurality of separate cavities and wherein each of said cavities has an interior area at least partially filled with said fill material.

11. The device of claim 6 wherein the housing is made from a flexible material.

12. The device of claim 6 wherein the housing is made of a resilient material that, after the device has been deformed, will act to at least partially cause the device to return to a shape it had prior to said deformation.

13. The device of claim 12 wherein the device is capable of attaining a spherical shape and is sized to fit within a user's palm.

14. The device of claim 6 wherein said fill material further includes a third dry material, wherein said third dry material acts as a lubricant and functions to increase the flowability of the fill material.

15. The device of claim 14 wherein said third dry material is in the form of a powder lubricant having a coefficient of friction substantially equal to that of talc.

16. The device of claim 6 wherein the housing has a rectangular shape.

17. The device of claim 6 wherein the fill material includes 16 parts of the first dry material mixed with about 1–3 parts of the second dry material.

18. A microwaveable heating device designed and adapted for use as a heating pad, said device comprising:

a dry fill material designed and adapted to be heated through the application of microwave energy to said dry mixture, wherein said mixture includes a first dry material composed of salt crystals, wherein said first dry material functions to retain heat, wherein when said first dry material is subjected to a predetermined amount of microwave energy, said first dry material will exhibit a first microwave energy absorption rate and then exhibit a first heat transfer rate, and wherein said fill material also includes a second dry material that physically contacts the first dry material, wherein said second dry material is capable of absorbing microwave energy at a faster rate than the first dry material, wherein when said second dry material is subjected to said predetermined amount of microwave energy, said second dry material will exhibit a microwave energy absorption rate that is greater than that of the first dry material and thereby functions to heat said first dry material; and an outer housing completely filled with said fill material.

* * * * *